United States Patent
McGuckin, Jr. et al.

(10) Patent No.: US 10,117,671 B2
(45) Date of Patent: *Nov. 6, 2018

(54) ROTATIONAL THROMBECTOMY DEVICE

(71) Applicant: Argon Medical Devices, Inc., Plano, TX (US)

(72) Inventors: James F. McGuckin, Jr., Radnor, PA (US); John D. Leedle, Philadelphia, PA (US); Thanu Anidhran, Downington, PA (US)

(73) Assignee: Argon Medical Devices Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,606

(22) Filed: Sep. 20, 2016

(65) Prior Publication Data

US 2017/0007290 A1 Jan. 12, 2017

Related U.S. Application Data

(60) Continuation of application No. 13/907,953, filed on Jun. 2, 2013, now Pat. No. 9,474,543, which is a continuation of application No. 13/276,398, filed on Oct. 19, 2011, now Pat. No. 8,465,511, which is a continuation of application No. 12/854,378, filed on Aug. 11, 2010, now Pat. No. 8,062,317, which is a division of application No. 11/017,112, filed on Dec. 20, 2004, now Pat. No. 7,819,887.

(60) Provisional application No. 60/628,623, filed on Nov. 17, 2004.

(51) Int. Cl.
A61B 17/3207 (2006.01)
A61M 25/09 (2006.01)
A61B 17/00 (2006.01)

(52) U.S. Cl.
CPC ........... *A61B 17/320758* (2013.01); *A61B 2017/00867* (2013.01); *A61B 2017/320733* (2013.01); *A61M 2025/09083* (2013.01)

(58) Field of Classification Search
CPC ........... A61B 17/320758; A61B 2017/320733; A61M 2025/09083
See application file for complete search history.

(56) References Cited

U.S. PATENT DOCUMENTS

| | | |
|---|---|---|
| 3,612,058 A | 10/1971 | Ackerman |
| 3,749,085 A | 7/1973 | Wilson |
| 4,579,127 A | 4/1986 | Haacke |
| 4,745,919 A | 5/1988 | Bundy |

(Continued)

FOREIGN PATENT DOCUMENTS

| | | |
|---|---|---|
| DE | 1075903 | 2/1960 |
| WO | 9838926 | 9/1998 |

(Continued)

*Primary Examiner* — Kathleen Holwerda
(74) *Attorney, Agent, or Firm* — IpHorgan Ltd.

(57) ABSTRACT

A rotatable thrombectomy wire for breaking up thrombus or other obstructive material comprising an inner core composed of a flexible material and an outer wire surrounding at least a portion of the inner core. The outer wire has a sinuous shaped portion at a distal region. The inner core limits the compressibility of the outer wire. The outer wire is operatively connectable at a proximal end to a motor for rotating the wire to macerate thrombus.

15 Claims, 4 Drawing Sheets

(56) References Cited

U.S. PATENT DOCUMENTS

| | | | |
|---|---|---|---|
| 4,883,460 A | 11/1989 | Zanetti | |
| 4,906,244 A | 3/1990 | Pinchuk et al. | |
| 4,984,581 A | 1/1991 | Stice et al. | |
| 4,990,134 A | 2/1991 | Auth | |
| 5,025,799 A | 6/1991 | Wilson | |
| 5,067,489 A | 11/1991 | Lind et al. | |
| 5,067,957 A | 11/1991 | Jervis | |
| 5,131,406 A | 7/1992 | Keltenback | |
| 5,203,772 A | 4/1993 | Hammerslag et al. | |
| 5,211,183 A | 5/1993 | Wilson | |
| 5,213,111 A | 5/1993 | Cook | |
| 5,217,026 A | 6/1993 | Stay | |
| 5,251,640 A | 10/1993 | Osborne | |
| 5,253,653 A | 10/1993 | Daigle | |
| 5,261,877 A | 11/1993 | Fine et al. | |
| 5,299,580 A | 4/1994 | Atkinson | |
| 5,312,427 A | 5/1994 | Shturman | |
| 5,313,967 A | 5/1994 | Lieber | |
| 5,314,438 A | 5/1994 | Shturman | |
| 5,333,620 A | 8/1994 | Moutafis et al. | |
| 5,341,818 A | 8/1994 | Abrams | |
| 5,345,945 A | 9/1994 | Hodgson | |
| 5,372,144 A | 12/1994 | Martier | |
| 5,376,100 A | 12/1994 | Lefebvre | |
| 5,452,726 A | 9/1995 | Burmeister | |
| 5,490,859 A | 2/1996 | Mische | |
| 5,501,694 A | 3/1996 | Ressemann et al. | |
| 5,514,128 A | 5/1996 | Hillsmon | |
| 5,540,707 A | 7/1996 | Ressemann et al. | |
| 5,551,443 A | 9/1996 | Sepetka | |
| 5,562,275 A | 10/1996 | Weissenfluh | |
| 5,569,179 A | 10/1996 | Adrian et al. | |
| 5,584,843 A | 12/1996 | Wulfman | |
| 5,605,162 A | 2/1997 | Mirzaee | |
| 5,653,722 A | 8/1997 | Kieturakis | |
| 5,746,701 A | 5/1998 | Noone | |
| 5,762,637 A | 6/1998 | Berg et al. | |
| 5,766,191 A | 6/1998 | Trerotola | |
| 5,797,856 A | 8/1998 | Frisbie et al. | |
| 5,833,631 A | 11/1998 | Nguyen | |
| 5,836,893 A | 11/1998 | Urick | |
| 5,840,046 A | 11/1998 | Deem | |
| 5,843,103 A | 12/1998 | Wulfman | |
| 5,885,227 A | 3/1999 | Finlayson | |
| 5,902,263 A | 5/1999 | Patterson | |
| 5,902,268 A | 5/1999 | Saab | |
| 5,910,364 A | 6/1999 | Miyata | |
| 5,916,166 A | 6/1999 | Reiss | |
| 5,924,998 A | 7/1999 | Cornelius | |
| 5,938,623 A | 8/1999 | Quiachon | |
| 5,971,991 A | 10/1999 | Sunderland | |
| 5,984,877 A | 11/1999 | Fleischhacker, Jr. | |
| 6,004,279 A | 12/1999 | Crowley | |
| 6,019,736 A | 2/2000 | Avellanet | |
| 6,080,117 A | 6/2000 | Cornelius | |
| 6,083,198 A | 7/2000 | Afzal | |
| 6,090,118 A | 7/2000 | McGuckin, Jr. | |
| 6,106,485 A | 8/2000 | McMahan | |
| 6,113,614 A | 9/2000 | Mears | |
| 6,165,140 A | 12/2000 | Ferrera et al. | |
| 6,168,570 B1 | 1/2001 | Ferrera et al. | |
| 6,185,449 B1 | 2/2001 | Berg | |
| 6,206,898 B1 | 3/2001 | Honeycutt et al. | |
| 6,217,589 B1 | 4/2001 | McAlister | |
| 6,217,595 B1 | 4/2001 | Shturman | |
| 6,251,085 B1 | 6/2001 | Tezuka | |
| 6,251,086 B1 | 6/2001 | Cornelius | |
| 6,254,550 B1 | 7/2001 | McNamara | |
| 6,319,262 B1 | 11/2001 | Bates et al. | |
| 6,371,928 B1 | 4/2002 | Mcfann | |
| 6,432,066 B1 | 8/2002 | Ferrera et al. | |
| 6,454,775 B1 | 9/2002 | Demarais et al. | |
| 6,454,779 B1 | 9/2002 | Taylor | |
| 6,458,127 B1 * | 10/2002 | Truckai | A61B 17/12022 606/213 |
| 6,475,226 B1 | 11/2002 | Belef | |
| 6,482,215 B1 | 11/2002 | Shiber | |
| 6,494,890 B1 | 12/2002 | Shturman | |
| 6,572,630 B1 | 6/2003 | McGuckin | |
| 6,579,299 B2 | 6/2003 | Jacobson | |
| 6,595,932 B2 | 7/2003 | Ferrera et al. | |
| 6,602,207 B1 | 8/2003 | Mam | |
| 6,602,262 B2 | 8/2003 | Griego et al. | |
| 6,602,264 B1 | 8/2003 | McGuckin | |
| 6,620,114 B2 | 9/2003 | Urba | |
| 6,620,179 B2 | 9/2003 | Boock | |
| 6,656,134 B2 | 12/2003 | Cornelius | |
| 6,660,014 B2 | 12/2003 | Demarais | |
| 6,663,613 B1 | 12/2003 | Evans et al. | |
| 6,669,652 B2 | 12/2003 | Anderson | |
| 6,673,025 B1 | 1/2004 | Richardson | |
| 6,702,830 B1 | 3/2004 | Demarais et al. | |
| 6,767,353 B1 | 7/2004 | Shiber | |
| 6,790,215 B2 | 9/2004 | Findlay | |
| 6,805,676 B2 | 10/2004 | Klint | |
| 6,824,545 B2 | 11/2004 | Sepetka et al. | |
| 6,881,194 B2 | 4/2005 | Miyata et al. | |
| 6,911,016 B2 | 6/2005 | Balzum et al. | |
| 6,929,633 B2 | 8/2005 | Evans | |
| 7,037,316 B2 | 5/2006 | McGuckin, Jr. et al. | |
| 7,074,197 B2 | 7/2006 | Reynolds et al. | |
| 7,115,101 B2 | 10/2006 | Cornelius et al. | |
| 7,309,318 B2 | 12/2007 | Cassell et al. | |
| 7,470,239 B1 | 12/2008 | Rooney et al. | |
| 7,494,687 B2 | 2/2009 | Cox | |
| 7,507,246 B2 | 3/2009 | McGuckin et al. | |
| 7,819,887 B2 * | 10/2010 | McGuckin, Jr. | A61B 17/320758 606/159 |
| 8,246,641 B2 | 8/2012 | Osborne et al. | |
| 8,414,543 B2 | 4/2013 | McGuckin et al. | |
| 8,465,511 B2 * | 6/2013 | McGuckin, Jr. | A61B 17/320758 606/159 |
| 2001/0009980 A1 | 7/2001 | Richardson et al. | |
| 2001/0031981 A1 | 10/2001 | Evans | |
| 2002/0013548 A1 | 1/2002 | Hinchliffe | |
| 2002/0095102 A1 | 7/2002 | Winters | |
| 2002/0165567 A1 | 11/2002 | Shiber | |
| 2002/0173812 A1 | 11/2002 | McGuckin, Jr. | |
| 2003/0023190 A1 | 1/2003 | Cox | |
| 2003/0139750 A1 | 7/2003 | Shinozuka et al. | |
| 2003/0181828 A1 | 9/2003 | Fujimato | |
| 2003/0191483 A1 * | 10/2003 | Cooke | A61B 17/320758 606/159 |
| 2003/0216668 A1 | 11/2003 | Howland | |
| 2004/0030266 A1 | 2/2004 | Murayama | |
| 2004/0167436 A1 | 8/2004 | Reynolds | |
| 2004/0167442 A1 | 8/2004 | Shireman | |
| 2004/0167443 A1 | 8/2004 | Shireman | |
| 2004/0181175 A1 | 9/2004 | Clayman | |
| 2004/0193073 A1 | 9/2004 | DeMello | |
| 2005/0004560 A1 | 1/2005 | Cox | |
| 2005/0054951 A1 | 3/2005 | Parins | |
| 2005/0055040 A1 | 3/2005 | Tal | |
| 2005/0137501 A1 | 6/2005 | Euteneuer et al. | |
| 2006/0074441 A1 | 4/2006 | McGuckin, Jr. et al. | |
| 2006/0106407 A1 | 5/2006 | McGuckin, Jr. et al. | |
| 2006/0142793 A9 | 6/2006 | Prudnikov et al. | |
| 2007/0088323 A1 | 4/2007 | Campbell et al. | |
| 2008/0319462 A1 | 12/2008 | Montague et al. | |
| 2010/0211087 A1 | 8/2010 | Osborne | |
| 2010/0305592 A1 | 12/2010 | McGuckin et al. | |
| 2011/0077673 A1 | 3/2011 | Grubac et al. | |
| 2011/0282370 A1 | 11/2011 | Levine et al. | |
| 2012/0035634 A1 | 2/2012 | McGuckin et al. | |

(56) References Cited

U.S. PATENT DOCUMENTS

2012/0116429 A1   5/2012   Levine et al.
2012/0239066 A1   9/2012   Levine et al.

FOREIGN PATENT DOCUMENTS

| WO | 9923958 | 5/1999 |
| WO | 9956638 | 11/1999 |
| WO | 0032265 | 6/2000 |
| WO | 0929430 | 3/2009 |

* cited by examiner

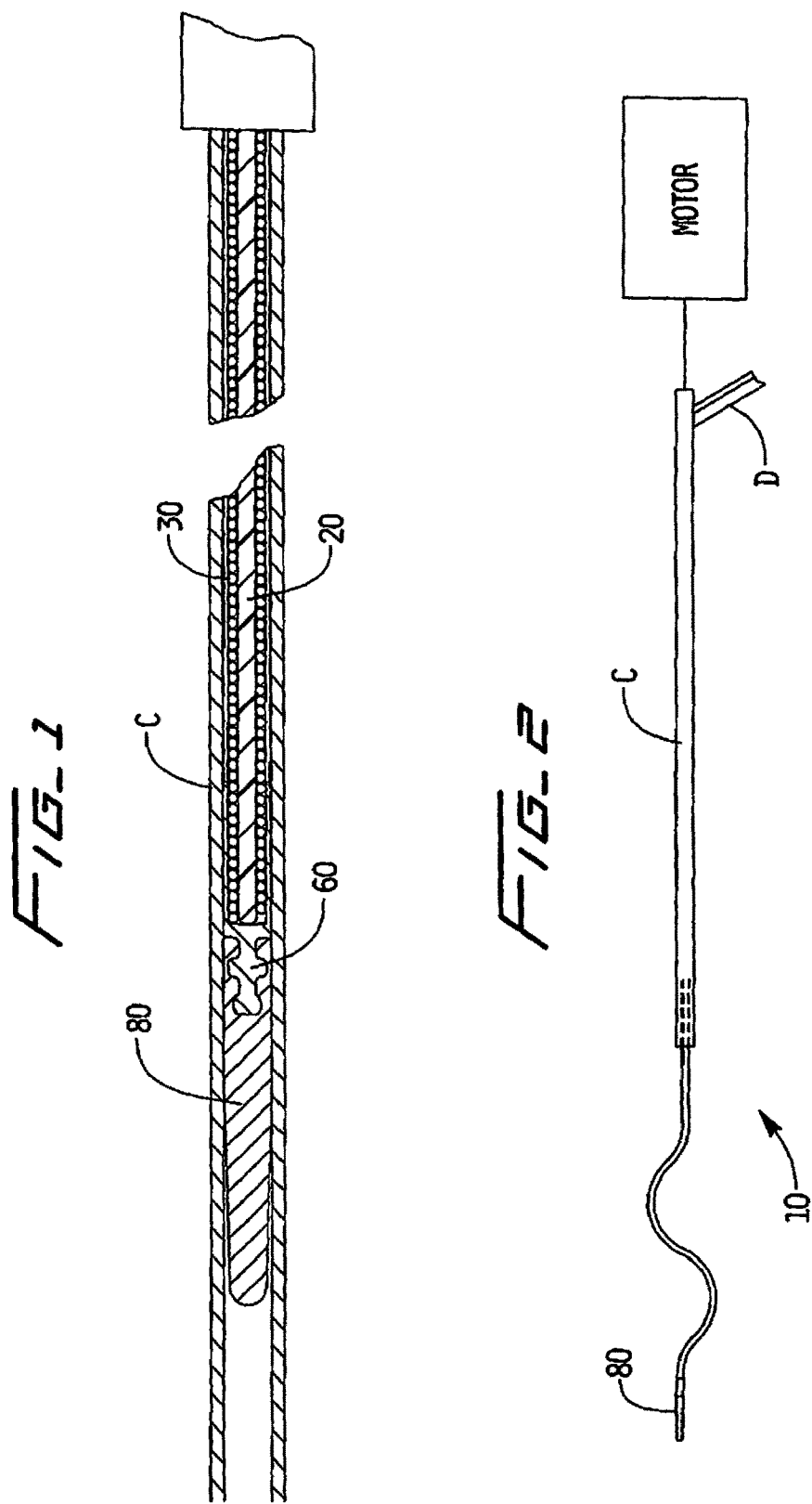

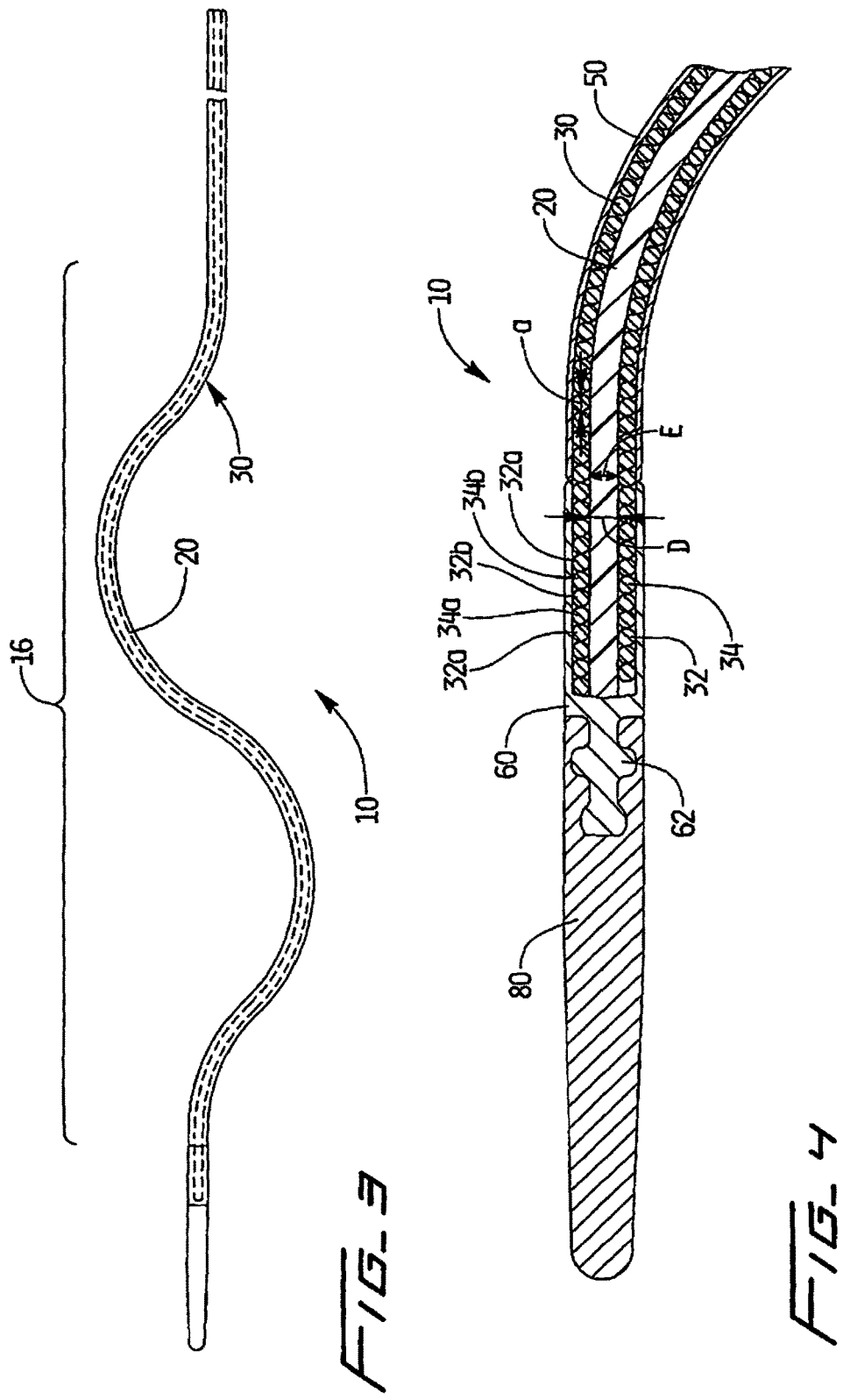

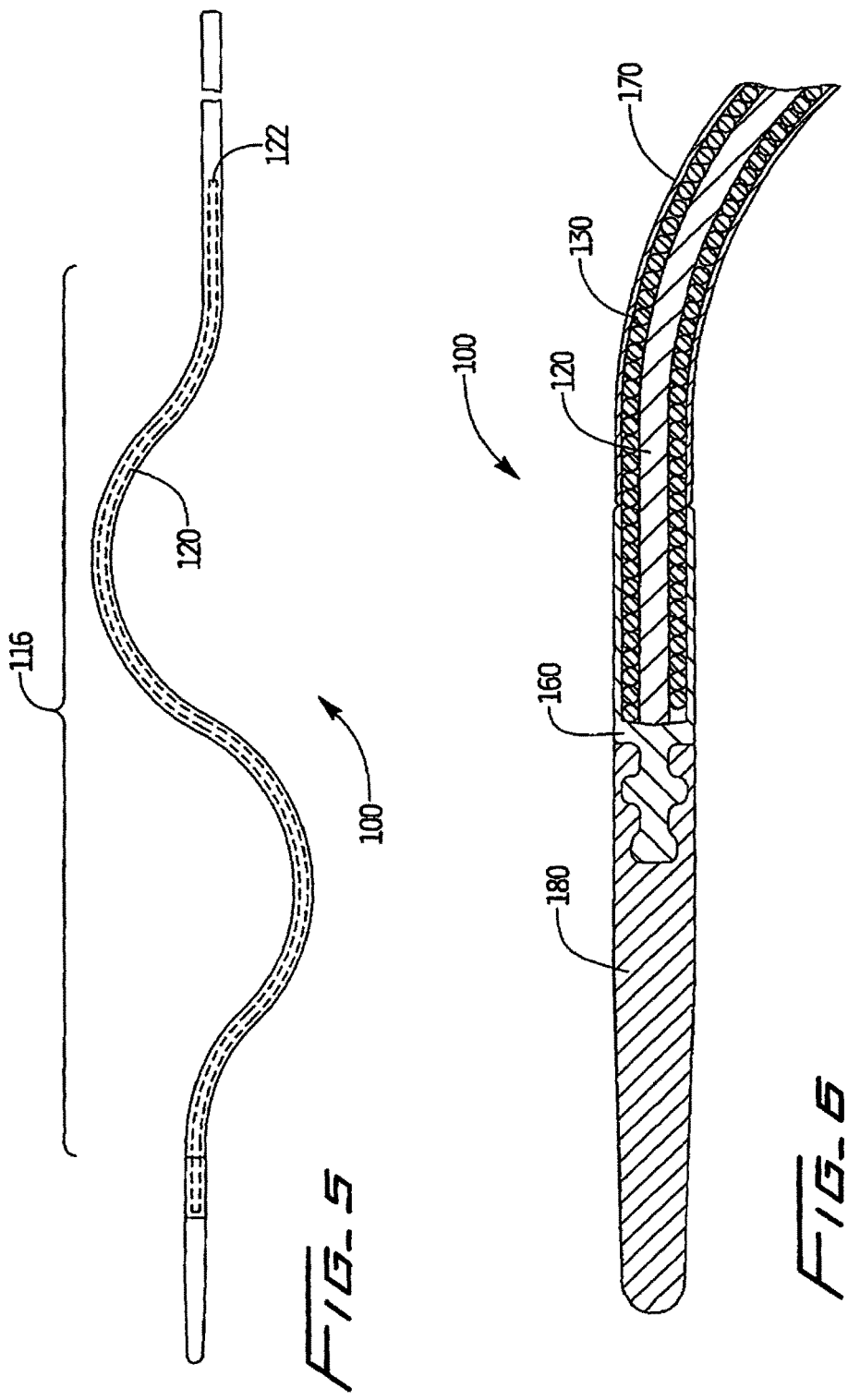

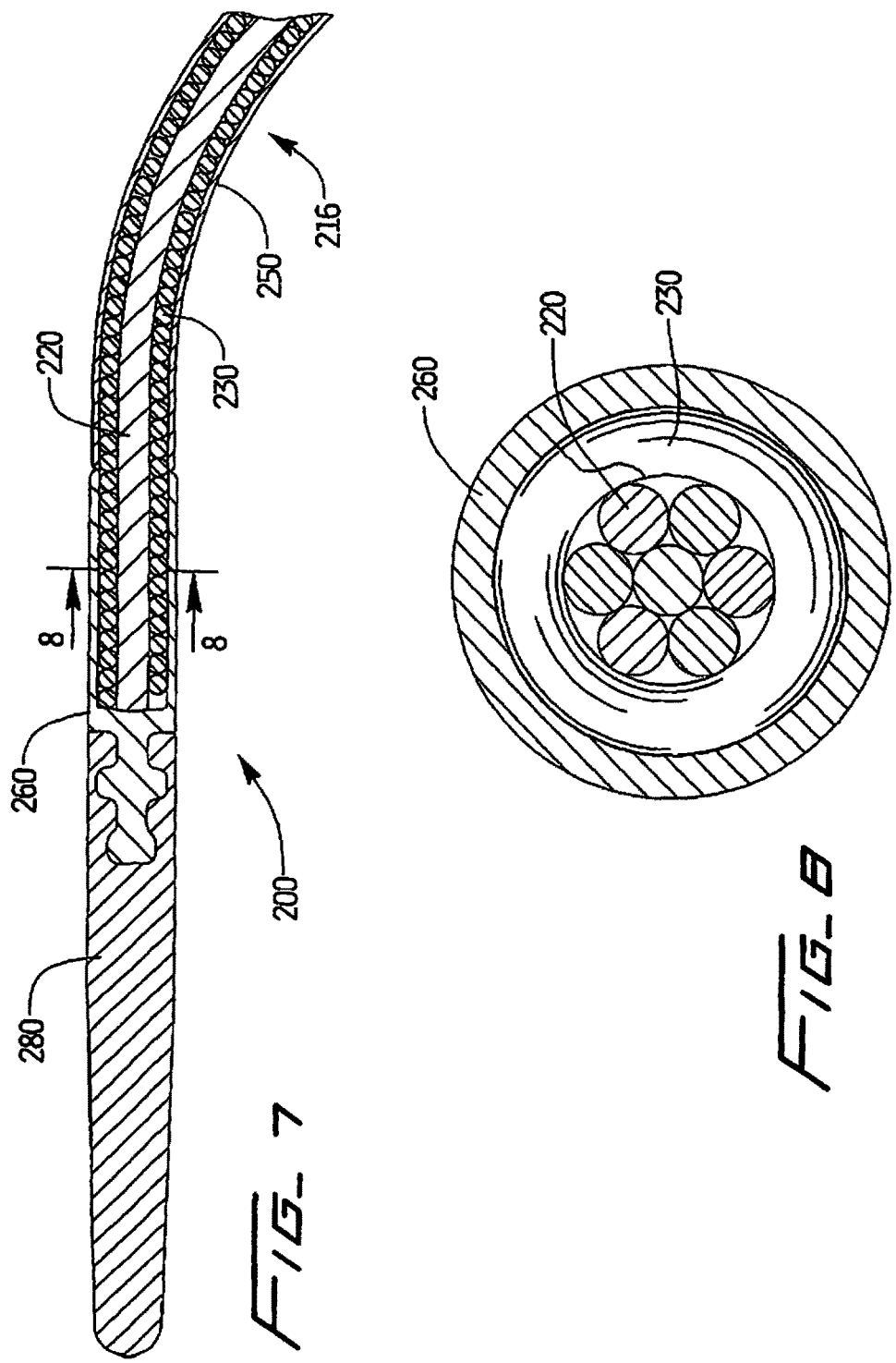

ROTATIONAL THROMBECTOMY DEVICE

This application is a continuation of application Ser. No. 13/907,953, filed on Jun. 2, 2013, which is a continuation of application Ser. No. 13/276,398, filed on Oct. 19, 2011, now U.S. Pat. No. 8,465,511, which is a continuation of application Ser. No. 12/854,378, filed on Aug. 11, 2010, now U.S. Pat. No. 8,062,317, which is a divisional of application Ser. No. 11/017,112, filed on Dec. 20, 2004, now U.S. Pat. No. 7,819,887, which claims benefit of provisional application Ser. No. 60/628,623, filed Nov. 17, 2004, the entire contents of each of these applications are incorporated herein by reference.

BACKGROUND

Technical Field

This application relates to a rotational thrombectomy wire for clearing thrombus from native vessels.

Background of Related Art

In one method of hemodialysis, dialysis grafts, typically of PTFE, are implanted under the patient's skin, e.g. the patient's forearm, and sutured at one end to the vein for outflow and at the other end to the artery for inflow. The graft functions as a shunt creating high blood flow from the artery to the vein and enables access to the patient's blood without having to directly puncture the vein. (Repeated puncture of the vein could eventually damage the vein and cause blood clots, resulting in vein failure.) One needle is inserted into the graft to withdraw blood from the patient for transport to a dialysis machine (kidney machine); the other needle is inserted into the graft to return the filtered blood from the dialysis machine to the patient. In the dialysis machine, toxins and other waste products diffuse through a semi-permeable membrane into a dialysis fluid closely matching the chemical composition of the blood. The filtered blood, i.e. with the waste products removed, is then returned to the patient's body.

Over a period of time, thrombus or clots may form in the graft. Thrombus or clots may also form in the vessel. One approach to break up these clots and other obstructions in the graft and vessel is the injection of thrombolytic agents. The disadvantages of these agents are they are expensive, require lengthier hospital procedures and create risks of drug toxicity and bleeding complications as the clots are broken.

U.S. Pat. No. 5,766,191 provides another approach to breaking up clots and obstructions via a mechanical thrombectomy device. The patent discloses a basket having six memory wires expandable to press against the inner lumen to conform to the size and shape of the lumen. This device could be traumatic if used in the vessel, could denude endothelium, create vessel spasms and the basket and drive shaft could fracture.

U.S. Pat. No. 6,090,118 discloses a mechanical thrombectomy device for breaking up clots. The single thrombectomy wire is rotated to create a standing wave to break-up or macerate thrombus. U.S. Patent Publication No. 2002/0173812 discloses another example of a rotational thrombectomy wire for breaking up clots. The thrombectomy wire has a sinuous shape at its distal end and is contained within a sheath in a substantially straight non-deployed position. When the sheath is retracted, the distal portion of the wire is exposed to enable the wire to return to its non-linear sinuous configuration. The wire is composed of stainless steel. Actuation of the motor causes rotational movement of the wire, creating a wave pattern, to macerate thrombus. The device of the '812 patent publication is effective in atraumatically and effectively breaking up blood clots in the graft and is currently being marketed by Datascope, Inc. as the Pro-Lumen* thrombectomy catheter. In the marketed device, the wire is a bifilar wire, composed of two stainless steel wires wound side by side with a metal tip and an elastomeric tip at the distalmost end.

Although the sinuous wire of the '812 publication is effective in proper clinical use to macerate thrombus in dialysis grafts, it is not suited for use in native vessels. The device is indicated for use in grafts, and if improperly used the wire can kink or knot, and perhaps even break. The wire can also bend, making it difficult to withdraw after use, and can lose its shape. Additionally, the wire would be abrasive to the vessel and the vessel could get caught in the interstices of the wire. It could also cause vessels spasms which can cause the vessel to squeeze down on the wire which could break the wire. Similar problems would occur with the use of the device of the '118 patent in native vessels.

The need therefore exists for a rotational thrombectomy wire which can be used to clear clots or other obstructions from the native vessels. Such wire could advantageously be used not only in native vessels adjacent dialysis grafts but for deep vein thrombosis and pulmonary embolisms.

SUMMARY

The present invention advantageously provides a rotational thrombectomy wire for breaking up thrombus or other obstructive material in a lumen of a native vessel.

The present invention provides a rotational thrombectomy wire comprising an inner core composed of a flexible material and a multifilar outer wire surrounding at least a portion of the inner core. The outer wire includes at least first and second metal wires wound side by side and having a sinuous shaped portion at a distal region. The inner core at a distal portion has a sinuous shaped portion within the sinuous portion of the outer wire. The inner core limits the compressibility of the multifilar wire. The multifilar wire is operatively connectable at a proximal end to a motor for rotating the wire to macerate thrombus within the vessel.

In a preferred embodiment, the inner core is composed of nylon material. In another embodiment, the inner core is composed of shape memory material wherein the inner core assumes its sinuous shape in the memorized configuration. In another embodiment, the core comprises at least two twisted wires of stainless steel.

The thrombectomy wire preferably further includes a polymeric material surrounding at least a distal portion of the multifilar wire. In a preferred embodiment, the polymeric material comprises a shrink wrap material attached to the multifilar wire. In another embodiment, the polymeric material is a coating over the multifilar wire.

The thrombectomy wire preferably comprises a flexible and blunt tip positioned at a distal end.

The inner core can have in one embodiment an enlarged distal end to form a connection portion and a metal tip secured to a distal end of the multifilar wire has a recess to receive the enlarged end of the inner core to frictionally engage the inner core.

In one embodiment, the first and second metal wires are wound together such that the coils of the first wire occupy the space between adjacent turns of the second wire and the coils of the multifilar outer wire have an inner diameter approximately equal to an outer diameter of the inner core.

The present invention also provides a rotatable thrombectomy wire for breaking up thrombus or other obstructive material in a lumen of a vessel comprising a multifilar outer wire including at least two metal wires wound side by side and operatively connectable at a proximal end to a motor for rotating the wire to macerate thrombus. The multifilar wire has a sinuous shaped portion at a distal region. A polymeric material surrounds at least a region of the sinuous portion of the multifilar outer wire to block the interstices of the multifilar wire.

In a preferred embodiment, the polymeric material comprises a shrink wrap material. In another embodiment, the polymeric material is a coating over the bifilar wire.

The present invention also provides a thrombectomy apparatus for breaking up thrombus or other obstructive material comprising a handle, a sheath, a battery, a motor powered by the battery, and a sinuous thrombectomy wire having at least one wire wound to form a coil and an inner core composed of a material to limit the compressibility of the coil. The coil has a sinuous portion and surrounds at least a distal region of the inner core. The inner core has a sinuous portion within the sinuous portion of the coil. The sinuous portion of the inner core and first and second wires are movable from a straighter configuration within the sheath for delivery to a sinuous configuration when exposed from the sheath.

In a preferred embodiment, a polymeric material surrounds at least a distal portion of the coil to cover the interstices of the coil. In one embodiment, the core is composed of a shape memory material wherein the memorized position of the core has a sinuous configuration. In another embodiment, the core is composed of Nylon. In another embodiment, the core is composed of at least two twisted wires of stainless steel.

The present invention also provides a method for breaking up thrombus or other obstructive material in a native vessel comprising:

providing a thrombectomy wire having an inner core composed of a flexible material and at least one outer wire surrounding at least a portion of the inner core, the outer wire has a sinuous shaped portion at a distal region and the inner core has a sinuous shaped portion within the sinuous portion of the outer wire, and a polymeric material surrounding at least a distal portion of the at least one outer wire to block the interstices of the at least one outer wire;

delivering the wire to the lumen of the native vessel such that the sinuous shaped portions of the inner core and bifilar outer wire are in a more linear configuration within a sheath;

exposing the sinuous portion of the inner core and the at least one outer wire; and actuating a motor operatively connected to the thrombectomy wire so the sinuous portion of the at least one outer wire contacts the inner wall of the native vessel to macerate thrombus in the vessel.

BRIEF DESCRIPTION OF THE DRAWINGS

Preferred embodiment(s) of the present disclosure are described herein with reference to the drawings wherein:

FIG. 1 is a side view in partial cross-section of a first embodiment of a thrombectomy wire of the present invention shown inside a catheter sleeve for delivery;

FIG. 2 is a schematic view illustrating motorized rotation of the wire and a port for fluid delivery;

FIG. 3 is a schematic side elevational view of the sinuous portion of the thrombectomy wire to depict a first embodiment of the inner core positioned therein;

FIG. 4 is an enlarged cross-sectional view of the distalmost region of the rotational thrombectomy wire of FIG. 3;

FIG. 5 is schematic side elevational view of the sinuous portion of the thrombectomy wire to depict a second embodiment of the inner core positioned therein; and FIG. 6 is an enlarged side view of the distalmost region of the rotational wire of FIG. 5;

FIG. 7 is a schematic side elevational view of the sinuous portion of the thrombectomy wire to depict a third embodiment of the inner core positioned therein; and FIG. 8 is a cross-sectional view taken along line 8-8 of FIG. 7.

DETAILED DESCRIPTION OF PREFERRED EMBODIMENTS

Referring now in detail to the drawings where like reference numerals identify similar or like components throughout the several views, FIGS. 3 and 4 illustrate a first embodiment of the thrombectomy wire of the present invention. The thrombectomy wire, designated generally by reference numeral 10, includes a core 20, a bifilar wire (coil) 30, and shrink wrap 50. The bifilar wire 30 is formed by two stainless steel wires 32, 34, wound together. As shown they are wound side by side so the cross-sectional area or diameter "a" of the wire fills the space between adjacent turns of the other wire. For example, turns 32a and 32b are filled by respective turns 34a, 34b as shown. Preferably the bifilar wire 30 has a length of about 30 inches and a diameter of about 0.030 inches to about 0.040 inches and more preferably about 0.035 inches. When used in deeper native vessels, e.g. deep veins of the legs or pulmonary circuit, the wire 30 can have a length of about 52 inches. Other dimensions are also contemplated.

The distal region 16 of the bifilar wire 30 is formed into a sinuous or s-shape to contact the vessel wall as the wire rotates.

Although in the preferred illustrated and described embodiments, the outer wire is a multifilar wire in the form of a bifilar wire (two wires), a different number of wires could be wound to form the outer wire component of the thrombectomy wire of the present invention. In yet another embodiment the outer wire can comprise a single wound wire.

The bifilar wire 30 is preferably cold formed into an over-formed s-shape. The bifilar wire is heated, for example at about 670 degrees Fahrenheit, which removes residual stresses and changes the shape of the "s" so it warps back to its desired shape. This stress relief process makes the wire more dimensionally stable.

A tip 80, preferably composed of rubber, Pebax, or other elastomeric materials, is mounted at the distalmost tip of the wire 10 to provide the wire 10 with an atraumatic distal tip to prevent damage to the vessel wall during manipulation and rotation of the wire. A metal lip 60 is attached by laser welding or other methods to the distal end of the bifilar wire 30. The metal tip 60 has an enlarged dumbbell shaped head 62 to facilitate attachment to tip 80. The flexible tip 80 is attached by injection molding over the machined tip. Other attachment methods are also contemplated.

With continued reference to FIG. 4, a core 20 is positioned within the bifilar wire 30 and preferably has an outer diameter E substantially equal to the inner diameter D of the coil. The core at a distal portion has a sinuous shaped portion within the sinuous shaped portion of the outer wire 30, corresponding to and formed by the sinuous shape of outer wire 30. In one embodiment, the core extends the entire length of the bifilar wire 30 and this is shown in the schematic drawing of FIG. 3. The core 20 can alternatively have a length of about 4-5 inches so it extends through the distal linear portion and sinuous portion of the wire 30. That is, in such embodiment, the core extends through the portion of the wire that is exposed from the sheath and used to macerate thrombus. It is also contemplated that the core can extend within a shorter or longer length of the bifilar wire.

The core 20 is composed of a flexible material which will limit the compressibility of the wire 30 during use. The core in the embodiment of FIG. 3 is composed of Nylon, and preferably a drawn Nylon monofilament. Other possible materials include, for example, Teflon, polypropylene, PET, and fluorocarbon. The Nylon provides a non-compressible material to limit the compressibility of the wire 30 during use. That is, as noted above, the Nylon core preferably has a diameter E to fill the inside of the coil 30, e.g. a diameter of about 0.008 inches to about 0.013 inches, and preferably about 0.012 inches. (Other dimensions are also contemplated.) This enables the coil (bifilar wire) 30 to compress only to that diameter. By limiting compressibility it strengthens the wire as it reduces its degree of elongation if it is under torque. It also prevents bending or knotting of the wire which could otherwise occur in native vessels. It increases the torsional strength of the wire and also strengthens the wire to accommodate spasms occurring in the vessel. An enlarged distal head, such as ball tip (not shown), can be provided on the core 20 to fit in a recess of machined tip 60. As an alternative, core 20 can be attached by adhesive at the tip, welded, crimped, soldered or can alternatively be free floating.

The shrink wrap material 50 covers a portion of the bifilar wire 30 proximal of the flexible tip 80 to block the interstices of the coil and provide a less abrasive surface. As shown in FIG. 4, the distal end of the shrink wrap abuts the proximal end of the tip 60. The shrink wrap can be made of PET, Teflon, Pebax, polyurethane or other polymeric materials. The material extends over the exposed portion of the wire 30 (preferably for about 3 inches to about 4 inches) and helps to prevent the native vessel from being caught in the coil and reduces vessel spasms. Alternatively, instead of shrink wrap, a coating can be applied to the coil formed by the bifilar wire to cover the interstices FIGS. 5 and 6 illustrate an alternate embodiment of the thrombectomy wire of the present invention, designated generally by reference numeral 100. Wire 100 is identical to wire 10 of FIG. 1, except for the inner core 120. It is identical in that it has a bifilar wire 130, a shrink wrap 170, an elastomeric tip 180 and metal, e.g. stainless steel, tip 160.

In this embodiment, the core 120 is composed of a shape memory material, preferably Nitinol (a nickel titanium alloy), which has a memorized configuration of a sinuous or s-shape substantially corresponding to the s-shape of the bifilar wire 130. In the softer martensitic state within the sheath, core 120 is in a substantially linear configuration. This state is used for delivering the wire to the surgical site. When the wire is exposed to warmer body temperature, the core 120 transforms to its austenitic state, assuming the s-shaped memorized configuration. Cold saline is delivered through the catheter during delivery to maintain the core 120 in this martensitic state; the warming occurs by exposure to body temperature to transform the core 120 to the memorized state. Such memorized s-shape helps maintain the s-shape of the bifilar wire 130 during use. Cold saline can also be delivered to the core 120 at the end of the procedure to facilitate withdrawal.

The Nitinol core 120, like the Nylon core 20, is not compressible so it will also limit the compressibility of the bifilar wire 130. The Nitinol core 120 also will increase the stiffness of the wire 100, thereby reducing the chance of knotting and kinking and increase the strength of the wire to accommodate any spasms in the vessel. Its shape memory helps hold the amplitude of the bifilar wire 130 during use to maintain its force against the clot for maceration upon rotation. It preferably extends about 4-5 inches so it extends through the distal linear portion and sinuous portion of the wire 130, terminating at end 122. Alternately it can extend a shorter or longer length within the wire 130, or even the entire length as shown in the schematic view of FIG. 5. It preferably has an outer diameter of about 0.008 inches to about 0.013 inches, and more preferably about 0.012 inches, corresponding to the inner diameter of the coil. Other dimensions are also contemplated.

In another embodiment, a stainless steel braid, cable, or strand of wires twisted together provides the inner core member to limit compressibility of the coil (bifilar wire) and provide increased stiffness, strength and other advantages of the core enumerated above. This is shown in the embodiment of FIGS. 7 and 8 where wire 200 has inner core 220 of seven twisted stainless steel wires. A different number of twisted wires is also contemplated. The other elements of the wire 200, e.g., outer bifilar wire 230, metal tip 260, tip 280 shrink wrap 250, etc., are the same as in wires 10 and 100 described herein.

The rotational thrombectomy wires 10, 100 and 200 of the present invention can be used with various thrombectomy catheters to macerate thrombus within the vessel. The rotational thrombectomy wire 10 (or wire 100 or 200) is contained within a flexible sheath or sleeve C of a catheter as shown in FIG. 1. Relative movement of the wire and sheath C will enable the wire 10 to be exposed to assume the curved (sinuous) configuration described below to enable removal of obstructions, such as blood clots, from the lumen of the vessel.

A motor powered by a battery is contained within a housing to macerate and liquefy the thrombus into small particles within the vessel lumen. This is shown schematically in FIG. 2. Wire 10 (or 100 or 200) is operatively connected to the motor. Operative connection encompasses direct connection or connection via interposing components to enable rotation when the motor is actuated. The curved regions of the wire 10 or (100 or 200) are compressed so the wire (including the distal region 16, 116 or 216, respectively) is in a substantially straight or linear non-deployed configuration when in the sheath C. This covering of the wire 10 (or 100 or 200) by sheath C facilitates insertion through an introducer sheath and manipulation within the vessel When the flexible sheath C is retracted, the wire is exposed to enable the wire to return to its non-linear substantially sinuous configuration for rotation about its longitudinal axis within the lumen of the vessel.

Fluids, such as imaging dye can be injected through the port D into the lumen of the sheath C in the space between wire 10 (or 100 or 200) and the inner wall of the sheath C, and exiting the distal opening to flow into the vessel. This imaging dye provides an indication that fluid flow has resumed in the vessel. The lumen of the sheath can also receive cold saline to cool the Nitinol core 120 as described above.

The rotational thrombectomy wires 10, 100 and 200 of the present invention can also be used with the thrombectomy catheters having one or more balloons such as the balloon described in the '812 publication. The wires 10, 100 and 200 can further be used with other thrombectomy catheters.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A rotational thrombectomy wire comprising:
   an inner core composed of a flexible material,
   an at least one outer wire wound over at least a portion of the inner core forming a coil;
   an exterior surface of the coil extending proximally of a distalmost end of the coil;
   the coil having a sinuous shaped portion;
   the inner core having a sinuous shaped portion within the sinuous shaped portion of the coil;
   a polymeric material positioned over the exterior surface of a first portion of the coil to block interstices of the at least one outer wire,
   a portion of a separate distal tip component positioned over the exterior surface of a second portion of the coil;
   a flexible polymeric tip positioned over the distal tip component and extending distally therefrom;
   the distal tip component extending distally of the distalmost end of the coil;
   the distal tip component extending proximally of a proximalmost end of the flexible polymeric tip; and
   the thrombectomy wire is operatively connectable to a motor for rotation by the motor.

2. The rotatable thrombectomy wire of claim 1, wherein the distal tip component includes a recess.

3. The rotatable thrombectomy wire of claim 2, wherein a portion of the inner core is within the recess.

4. The rotatable thrombectomy wire of claim 2, wherein a portion of the coil is within the recess.

5. The rotatable thrombectomy wire of claim 4, wherein the coil is welded to the distal tip component.

6. The rotatable thrombectomy wire of claim 1, wherein the at least one outer wire comprises a bifilar wire formed by first and second wires wound together side by side so a diameter of the first wire fills a space between adjacent turns of the second wire.

7. The rotatable thrombectomy wire of claim 1, wherein the distal tip component is composed of stainless steel.

8. The rotatable thrombectomy wire of claim 1, wherein the flexible polymeric tip is injection molded over the distal tip component.

9. The rotatable thrombectomy wire of claim 1, wherein the distal tip component contains a dumbbell shaped region.

10. The rotatable thrombectomy wire of claim 9, wherein the flexible polymeric tip is positioned over the dumbbell shaped region.

11. The rotatable thrombectomy wire of claim 10, wherein the flexible polymeric tip is injection molded over the dumbbell shaped region.

12. The rotatable thrombectomy wire of claim 1, wherein the inner core includes multiple wires twisted together.

13. The rotatable thrombectomy wire of claim 1, wherein the polymeric material is applied as a coating.

14. The rotatable thrombectomy wire of claim 1, wherein the polymeric material is applied as a shrink wrap material.

15. The rotatable thrombectomy wire of claim 1, wherein the inner core is composed of nylon material.

* * * * *